(12) United States Patent
Dey

(10) Patent No.: US 12,070,310 B2
(45) Date of Patent: Aug. 27, 2024

(54) DEVICE FOR THE CONTINUOUS AND NON-INVASIVE MONITORING OF BILIRUBIN IN REAL-TIME

(71) Applicant: IBRUM TECHNOLOGIES, Karnataka (IN)

(72) Inventor: Nibedit Dey, Bangalore (IN)

( * ) Notice: Subject to any disclaimer, the term of this patent is extended or adjusted under 35 U.S.C. 154(b) by 682 days.

(21) Appl. No.: 17/260,548

(22) PCT Filed: Jul. 30, 2019

(86) PCT No.: PCT/IN2019/050557
§ 371 (c)(1),
(2) Date: Jan. 14, 2021

(87) PCT Pub. No.: WO2020/026267
PCT Pub. Date: Feb. 6, 2020

(65) Prior Publication Data
US 2021/0267507 A1 Sep. 2, 2021

(30) Foreign Application Priority Data

Aug. 1, 2018 (IN) .............................. 201841029014

(51) Int. Cl.
*A61B 5/145* (2006.01)
*A61B 5/00* (2006.01)
*A61B 5/1455* (2006.01)

(52) U.S. Cl.
CPC ........ *A61B 5/14546* (2013.01); *A61B 5/1455* (2013.01); *A61B 5/4283* (2013.01)

(58) Field of Classification Search
CPC . A61B 5/14546; A61B 5/1455; A61B 5/4283; A61B 5/14551; A61B 5/01; A61B 5/4244; A61B 2503/04
See application file for complete search history.

(56) References Cited

U.S. PATENT DOCUMENTS 5,372,136 A 12/1994 Steuer et al.
6,615,064 B1 9/2003 Aldrich
(Continued)

FOREIGN PATENT DOCUMENTS

WO 2012/136982 A1 10/2012
WO 2015/081299 A2 6/2015

OTHER PUBLICATIONS

International Search Report in PCT Application No. PCT/IB2019/055701, dated Nov. 20, 2019.

*Primary Examiner* — Eric F Winakur
*Assistant Examiner* — Abid A Mustansir
(74) *Attorney, Agent, or Firm* — Nasr Patent Law LLC; Faisal K. Abou-Nasr

(57) ABSTRACT

A device for the continuous and real-time monitoring of bilirubin, comprises a housing that encloses a waterproof/splash proof body. The body comprises a bilirubin and temperature measuring module; a wearable biocompatible strap; a buckle; a display unit; a safety module; a learning module; a battery and charging unit; a switch; and a wireless connectivity facilitator. The bilirubin and temperature measuring module comprises: one or more light emitting sources; a microprocessor; one or more photodetectors; a filter; and an analogue to digital converter. The device can be configured to be mounted on a patient's wrist or any other body part like palm, earlobe, cheek, finger, forehead, and feet.

8 Claims, 3 Drawing Sheets

(56) References Cited

U.S. PATENT DOCUMENTS

| | | | |
|---|---|---|---|
| 6,671,528 B2 | 12/2003 | Steuer et al. | |
| 2005/0043606 A1* | 2/2005 | Pewzner | A61B 5/1455 |
| | | | 600/407 |
| 2011/0060200 A1 | 3/2011 | Bernreuter et al. | |
| 2011/0152637 A1* | 6/2011 | Kateraas | A61B 5/02055 |
| | | | 600/301 |
| 2012/0150047 A1* | 6/2012 | Terumoto | A61B 5/02427 |
| | | | 600/479 |
| 2014/0278229 A1* | 9/2014 | Hong | H04W 4/027 |
| | | | 702/160 |
| 2017/0014035 A1* | 1/2017 | Newberry | A61B 90/96 |
| 2020/0363360 A1* | 11/2020 | Smith | G01R 19/257 |
| 2021/0236844 A1* | 8/2021 | Jain | A61N 5/0621 |

* cited by examiner

DEVICE FOR THE CONTINUOUS AND NON-INVASIVE MONITORING OF BILIRUBIN IN REAL-TIME

CROSS-REFERENCE TO RELATED APPLICATIONS

This application is a 35 U.S.C. § 371 national stage application of PCT International Application No. PCT/IN2019/050557, filed on Jul. 30, 2019, which claims the benefit of Indian Application No. 201841029014, filed Aug. 1, 2018, the contents of which are hereby incorporated by reference in their entirety.

FIELD OF THE INVENTION

The present disclosure is generally related to a device for the monitoring of bilirubin. Particularly, it is related to a device for the continuous and non-invasive monitoring of bilirubin, said monitoring occurring in a real-time basis.

BACKGROUND OF THE INVENTION

Severe hyperbilirubinemia can lead to acute bilirubin encephalopathy or kernicterus. Hyperbilirubinemia is a condition in which there is too much bilirubin in the blood. When red blood cells break down, a substance called bilirubin is formed. Babies are not easily able to get rid of the bilirubin and it can build up in the blood and other tissues and fluids of the baby's body. Since bilirubin has a pigment, it causes a yellowing of the baby's skin, eyes, and other tissues. This is called jaundice. Depending on the cause of the hyperbilirubinemia, jaundice may appear at birth or at any time afterward. Although low levels of bilirubin are not usually a concern, large amounts can circulate to tissues in the brain and may cause seizures and brain damage. This is a condition called kernicterus.

Management of jaundiced neonates often requires measurement of total serum bilirubin (TSB). Total serum bilirubin is commonly determined by spectrophotometric methods by analysing plasma or serum sample. The measurement of serum bilirubin is gold standard but is an invasive procedure. Such techniques require drawing of blood causing pain and trauma to the neonate. In addition, there is a wide range of intra- and inter-laboratory variability in the performance of the bilirubin analysers.

Checking bilirubin levels after birth at pre-defined intervals involves multiple time needle pricks. Often, phototherapy units are not available in the same hospital where a baby is delivered. So, the baby is taken away from the mother to a different hospital or to a different city. Due to this, the family has to travel between the hospital in which the mother is present and the children's hospital. There is no point-of-care system that is available which measures the baby's bilirubin level at bedside or at home at certain pre-defined intervals.

There is, therefore, a need in the art for a device that monitors bilirubin continuously and non-invasively in real-time.

SUMMARY OF THE INVENTION

A device for the continuous and real-time monitoring of bilirubin is disclosed. The device comprises a housing that encloses a waterproof/splash proof body.

The body comprises a bilirubin and temperature measuring module; a wearable biocompatible strap; a buckle; a display unit; a safety module; a learning module; a battery and charging unit; a switch; and a wireless connectivity facilitator.

The bilirubin and temperature measuring module comprises: one or more light emitting sources that emit visible light radiations of multiple wavelengths and infrared light; a microprocessor that is configured to monitor and control the functioning of the device; one or more photodetectors to detect, collect, and amplify the reflected light from a patient's body; a filter that removes unwanted noise; and an analogue to digital converter, the output of which is processed to get the bilirubin level in real-time.

The wearable biocompatible strap is adjustable and detachable, and is configured to mount the device on a patient, with said biocompatible strap being single use or multi-use.

The display unit comprises an indicator light that is disposed on a top portion of the device, and displays the current level of bilirubin at certain pre-defined intervals in real-time, along with the degree of severity.

The learning module is configured to analyse the measured bilirubin levels at the current settings and recommend the best settings, thereby facilitating the changing of phototherapy settings without human intervention.

The battery and charging unit comprises a rechargeable battery.

The switch is used for powering the device on or off.

The wireless connectivity facilitator facilitates the device to provide feedback in real-time based on measured bilirubin concentration and body temperature to a central nursing station, a compatible phototherapy unit, an application on a handheld device and/or an application on a wearable device.

DETAILED DESCRIPTION OF THE INVENTION

Throughout this specification, the use of the word "comprise" and variations such as "comprises" and "comprising" implies the inclusion of an element or elements not specifically recited.

Throughout this specification, the disclosure of any range is to be construed as being inclusive of the lower limit of the range and the upper limit of the range.

Figure 1:
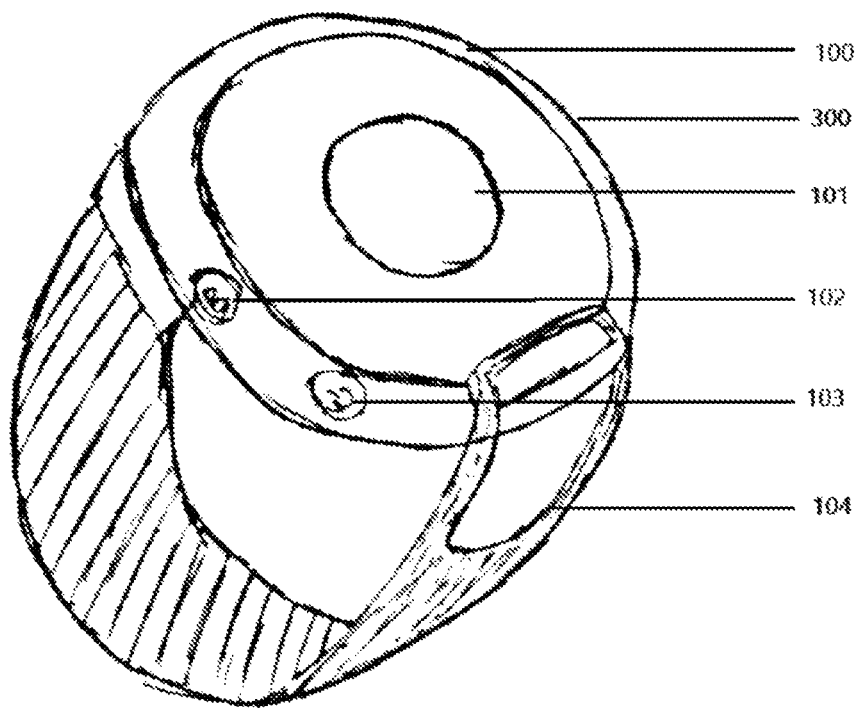
FIG. 1 illustrates an embodiment of a device for the continuous and non-invasive monitoring of bilirubin in real-time
Figure 2:
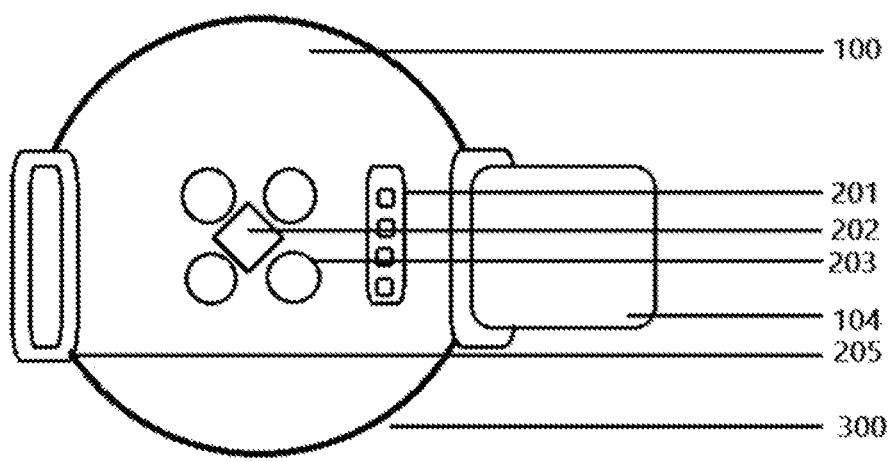
FIG. 2 illustrates a bottom view of an embodiment of a device for the continuous and non-invasive monitoring of bilirubin in real-time

As shown in FIG. 1 and FIG. 2, a device (300) for the continuous and real-time monitoring of bilirubin is disclosed. The device (300) comprises a housing that encloses a waterproof/splash proof body, said body comprising: a bilirubin and temperature measuring module (100); a wearable biocompatible strap (104) that is adjustable; a buckle (205); a display unit (101); a safety module; a learning module; a battery and charging unit (201); a switch for powering the device on or off (103); and a wireless connectivity facilitator (102).

The bilirubin and temperature measuring module (100) comprises: one or more light emitting sources (203) that emit visible light radiations of multiple wavelengths and infrared light; a microprocessor that is configured to monitor and control the functioning of the device (300); one or more photodetectors to detect, collect, and amplify the reflected light from a patient's body, said one or more photodetectors (202) being disposed in close proximity to the one or more light emitting sources (203), and being separated from the one or more light emitting sources (203) by a blocking channel; a filter that removes unwanted noise; and an analogue to digital converter, the output of which is processed to get the bilirubin level in real-time.

The light radiations span the wavelength between 350 nm and 1200 nm. The wavelength of at least one light radiation corresponds to the isosbestic point (a specific wavelength, wavenumber, or frequency at which the total absorbance of a sample does not change during a chemical reaction or a physical change of the sample) of bilirubin absorption and, therefore, is affected by the concentration of the bilirubin in the patient's blood stream.

In an embodiment of the present disclosure, the device is configured to have an isosbestic point at 470 nm.

In another embodiment of the present disclosure, the one or more light emitting sources are light emitting diodes (LEDs).

In yet another embodiment of the present disclosure, the safety module is an electrostatic discharge suppressor unit.

In yet another embodiment of the present disclosure, the safety module is a transient voltage suppression diode.

LEDs at different wavelength are used to measure different parameters which can act as noise. The different parameters, which include, but are not limited to, melanin, oxygenated haemoglobin, deoxyhaemoglobin, glycated haemoglobin, bilirubin, water, and albumin, are separated by using emitters of different wavelengths.

The display unit (101) comprises an indicator light that is disposed on a top portion of the device (300), and displays the current level of bilirubin at certain pre-defined intervals in real-time, along with the degree of severity. The indicator light is a low intensity light which doesn't cause any biological damage to tissues, or does not interfere with a phototherapy unit.

In yet another embodiment of the present disclosure, the display unit (101) displays the current level of bilirubin through pre-defined color indicators based on the range of bilirubin.

Based on the degree of severity, the device (300) may also send out one or more alerts to a user. The alert may be any type of alert known in the art and includes, but is not limited to, visual alerts, text messages, and sound alerts.

Figure 3:
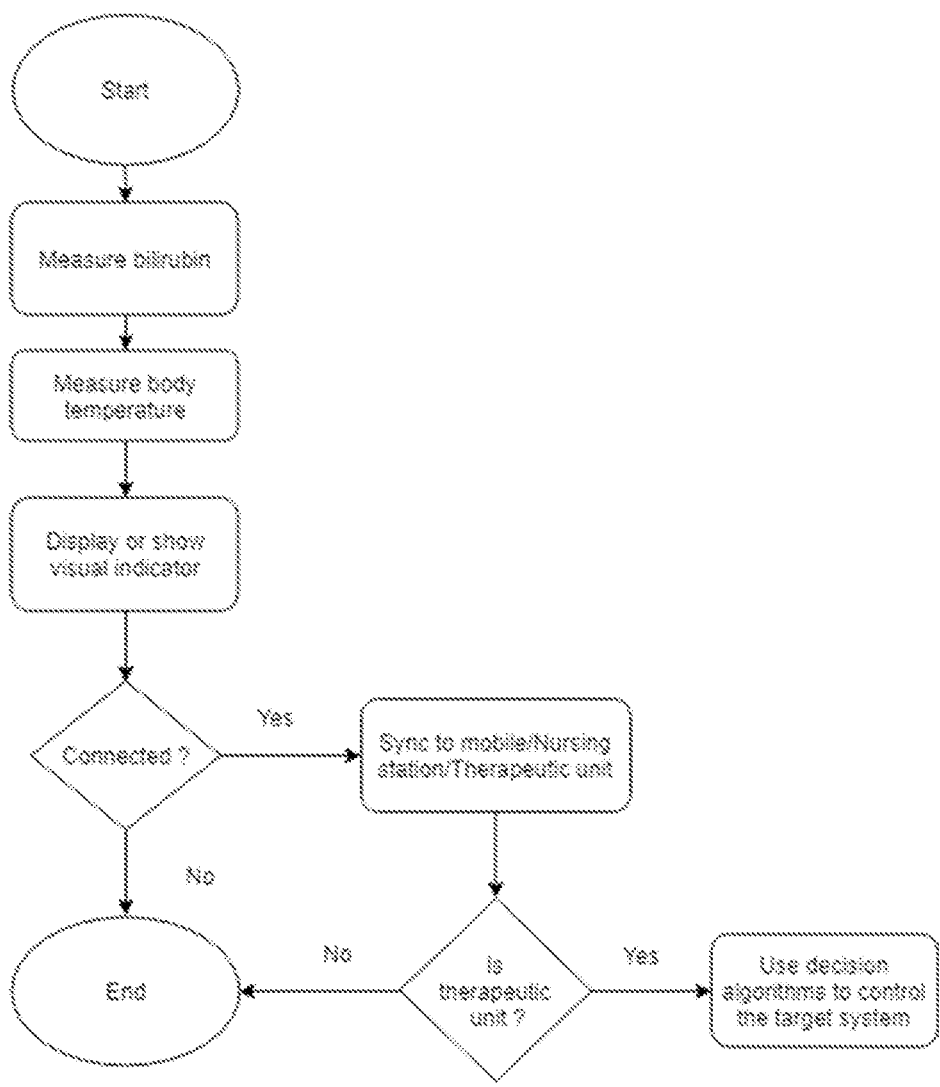
FIG. 3 depicts a flowchart of the feedback mechanism

As shown in FIG. 3, the device (300) monitors the bilirubin concentration and body temperature in real-time periodically at certain pre-defined intervals and provides feedback through the wireless connectivity facilitator (102) to a central nursing station, where it may be viewed by one or more healthcare professionals. The device (300) may record and store the data in an internal storage and/or external storage.

The feedback through the wireless connectivity facilitator (102) may also be transmitted to an application on a handheld device, an application on a wearable device, and/or a compatible phototherapy unit. Based on the feedback, the device (300) may also be controlled through the application on the handheld device, the application on the wearable device, and/or the compatible phototherapy unit. The data from the handheld device, the wearable device, and/or the compatible phototherapy unit may also be transmitted to the cloud for storage and/or backup purposes.

The handheld or the wearable device includes, but is not limited to, mobile phones, smart phones, tablets, phablets, and smart watches. The transmission of the real-time data through the wireless connectivity facilitator (102) may occur through wireless internet, mobile data, Bluetooth Low Energy, or the like.

The device (300) is capable of determining the effectiveness of phototherapy from the measured data. If the device (300) is connected to the compatible phototherapy unit and an intelligent mode is turned on through the application on the handheld or the wearable device, it can provide intelligent feedback with regards to the effectiveness at the current settings.

The learning module is configured to analyse the effectiveness of an ongoing therapy at the current settings and recommend the best settings. This facilitates the changing of phototherapy settings without human intervention, which can substantially improve the treatment time. The settings may also be transmitted from a cloud server to the device after analysis.

As illustrated in FIG. 3, the learning module analyses measured bilirubin data with time. If a reduction in bilirubin level is not detected, it requests the phototherapy unit to change the settings. On the other hand, if the bilirubin level has been detected as being under control, it recommends a reduction in the intensity.

The learning module gives output results as per a calibrated or standardised value. The output data can be used by compatible phototherapy units to change light intensity by selectively turning off or turning on LEDs on the phototherapy units.

The biocompatible wrist strap (104) is detachable and is configured to mount the device (300) on a patient. Further, the biocompatible strap (104) may be single use or multi-use. The device (300) is powered by a rechargeable battery that allows monitoring of the bilirubin in real-time for several days without need of charging and can be charged through a magnetic charger, wireless charger, or any other means known in the art.

The device (300) can be configured to be mounted on a patient's wrist or any other body part like palm, earlobe, cheek, finger, forehead, and feet. The device (300) may optionally measure and display oxygen saturation and glycated haemoglobin, and may be sterilized with or without the wearable biocompatible strap (104), depending on whether the strap (104) is single-use or multi-use.

It will be apparent to a person skilled in the art that the above description is for illustrative purposes only and should not be considered as limiting. Various modifications, additions, alterations and improvements without deviating from the spirit and the scope of the disclosure may be made by a person skilled in the art. Such modifications, additions, alterations and improvements should be construed as being within the scope of this disclosure.

LIST OF REFERENCE NUMERALS

100—Bilirubin and Temperature Measuring Module
101—Display Unit
102—Wireless Connectivity Facilitator
103—Power Switch
104—Wearable Biocompatible Strap
201—Battery and Charging Unit
202—One or More Photodetectors
203—One or More Light Emitting Sources
205—Buckle
300—Device for the Continuous and Real-time Monitoring of Bilirubin

I claim:

1. A device for the continuous and real-time monitoring of bilirubin, comprising:
   a housing that encloses a waterproof/splash proof body, said body comprising:
   a bilirubin and temperature measuring module that comprises:
      one or more light emitting sources that emit visible light radiations of multiple wavelengths and infrared light, said multiple wavelengths ranging between 350 nm and 1,200 nm, with the wavelength of at least one light radiation corresponding to the isosbestic point of bilirubin absorption;
      a microprocessor that is configured to monitor and control the functioning of the device;
      one or more photodetectors to detect, collect, and amplify the reflected light from a patient's body, said one or more photodetectors being disposed in close proximity to the one or more light emitting sources, and being separated from the one or more light emitting sources by a blocking channel; and
      a filter that removes unwanted noise, and an analogue to digital converter, the output of which is processed to get the bilirubin level in real-time, wherein the one or more light sources include emitters at different wavelengths configured to separately measure the unwanted noise caused by different parameters including melanin, oxygenated haemoglobin, deoxyhaemoglobin, glycated haemoglobin, water, and albumin;
   a wearable biocompatible strap that is adjustable and detachable, said biocompatible strap being configured to mount the device on a patient, with said biocompatible strap being single use or multi-use;
   a buckle;
   a display unit comprising an indicator light that is disposed on a top portion of the device, said display unit displaying the current level of bilirubin at certain pre-defined intervals in real-time, along with the degree of severity, with said indicator light being a low intensity light which doesn't cause any biological damage to tissues, or does not interfere with a phototherapy unit;
   a safety module;
   a learning module that is configured to analyse the effectiveness of an ongoing therapy at the current settings and recommend the best settings, thereby facilitating the changing of phototherapy settings without human intervention;
   a battery and charging unit that comprises a rechargeable battery;
   a switch for powering the device on or off; and
   a wireless connectivity facilitator that facilitates the device to provide feedback in real-time based on measured bilirubin concentration and body temperature to a central nursing station, a compatible phototherapy unit, an application on a handheld device and/or an application on a wearable device.

2. The device for the continuous and real-time monitoring of bilirubin as claimed in claim 1, wherein the device is configured to have an isosbestic point at 470 nm.

3. The device for the continuous and real-time monitoring of bilirubin as claimed in claim 1, wherein the one or more light emitting sources are light emitting diodes.

4. The device for the continuous and real-time monitoring of bilirubin as claimed in claim 1, wherein the device sends out one or more alerts to a user.

5. The device for the continuous and real-time monitoring of bilirubin as claimed in claim 1, wherein the device is controlled through the application on the handheld device, the application on the wearable device, and/or the compatible phototherapy unit.

6. The device for the continuous and real-time monitoring of bilirubin as claimed in claim 1, wherein the device is configured to be mounted on a patient's wrist, palm, earlobe, cheek, finger, forehead, or feet.

7. The device for the continuous and real-time monitoring of bilirubin as claimed in claim 1, wherein the device measures and displays oxygen saturation and glycated haemoglobin.

8. The device for the continuous and real-time monitoring of bilirubin as claimed in claim 1, wherein the device is sterilisable with or without the wearable biocompatible strap, depending on whether the strap is single-use or multi-use.

* * * * *